(12) United States Patent
Sidebotham

(10) Patent No.: US 7,169,185 B2
(45) Date of Patent: Jan. 30, 2007

(54) CANINE ACETABULAR CUP

(75) Inventor: Christopher G. Sidebotham, Mendham, NJ (US)

(73) Assignee: Impact Science and Technology, Inc., Mendham, NJ (US)

( * ) Notice: Subject to any disclaimer, the term of this patent is extended or adjusted under 35 U.S.C. 154(b) by 229 days.

(21) Appl. No.: 10/853,970

(22) Filed: May 26, 2004

(65) Prior Publication Data

US 2005/0267585 A1    Dec. 1, 2005

(51) Int. Cl.
*A61F 2/32* (2006.01)
(52) U.S. Cl. .................. 623/22.21; 623/22.28
(58) Field of Classification Search ............. 623/22.21, 623/22.28, 22.15–22.2, 22.23, 22.24–22.27, 623/22.31–22.33, 22.42
See application file for complete search history.

(56) References Cited

U.S. PATENT DOCUMENTS

| | | | | |
|---|---|---|---|---|
| 3,855,638 A | | 12/1974 | Pillar ............................ 3/1 |
| 4,172,296 A | * | 10/1979 | D'Errico .................. 623/22.28 |
| 4,550,448 A | | 11/1985 | Kenna ........................ 623/16 |
| 4,666,450 A | | 5/1987 | Kenna ........................ 623/22 |
| 4,715,859 A | * | 12/1987 | Schelhas et al. ......... 623/22.27 |
| 4,715,860 A | | 12/1987 | Amstutz et al. ............... 623/22 |
| 4,878,916 A | * | 11/1989 | Rhenter et al. .......... 623/22.24 |
| 4,904,265 A | | 2/1990 | MacCollum et al. ......... 623/22 |
| 5,021,062 A | * | 6/1991 | Adrey et al. ............. 623/22.36 |
| 5,047,056 A | | 9/1991 | Kenna ........................ 623/18 |
| 5,092,897 A | * | 3/1992 | Forte ....................... 623/22.18 |
| 5,226,917 A | | 7/1993 | Schryver ..................... 623/22 |
| 5,290,315 A | | 3/1994 | DeCarlo, Jr. ................ 623/22 |
| 5,310,408 A | * | 5/1994 | Schryver et al. ......... 623/22.37 |
| 5,370,704 A | * | 12/1994 | DeCarlo, Jr. ............. 623/22.22 |
| 5,549,696 A | * | 8/1996 | Willi ....................... 623/22.28 |
| 5,549,701 A | * | 8/1996 | Mikhail .................... 623/22.21 |
| 5,766,260 A | | 6/1998 | Whiteside .................... 623/22 |
| 5,874,123 A | | 2/1999 | Park .......................... 427/2.24 |
| 5,876,446 A | | 3/1999 | Agrawal et al. .............. 623/11 |
| 5,879,404 A | | 3/1999 | Bateman et al. .............. 623/22 |
| 5,879,405 A | | 3/1999 | Ries et al. .................... 623/22 |
| 6,066,176 A | * | 5/2000 | Oshida .................... 623/23.62 |
| 6,152,961 A | | 11/2000 | Ostiguy, Jr. et al. ..... 623/22.28 |

(Continued)

FOREIGN PATENT DOCUMENTS

EP    0501207 A1 *  2/1992

(Continued)

*Primary Examiner*—Alvin J. Stewart
(74) *Attorney, Agent, or Firm*—Ernest D. Buff & Associates, LLC; Ernest D. Buff; Theodore J. Pierson

(57) ABSTRACT

A plurality of canine acetabular cups designed to fit within different sized spherical reamed bone cavities to produce controlled interference without use of cements, screws or nails. Each of the canine acetabular cups, regardless of size, mates with a common femoral head, providing interchangeability. The controlled interference is obtained through use of a multiple curvature Ti—Al—V shell having a porous coating. The interference starts from zero at 50 degrees from the apex of the shell and extends to full interference value at 90 degrees from the apex. The Ti—Al—V shell carries a UHMW polyethylene insert, which is locked by interference, a non-circular post mated with an elongated opening and a circumferential locking groove mated with an interior projection. Initial stability is provided immediately after surgery due to the interference arrangement; long term stability is afforded by bone ingrowth.

8 Claims, 6 Drawing Sheets

U.S. PATENT DOCUMENTS

| | | |
|---|---|---|
| 6,203,844 B1 | 3/2001 | Park .......................... 427/2.26 |
| 6,368,354 B2 * | 4/2002 | Burstein et al. ......... 623/22.28 |
| 6,425,921 B1 * | 7/2002 | Grundei et al. .......... 623/22.15 |
| 6,558,428 B2 | 5/2003 | Park ........................ 623/23.59 |
| 6,827,742 B2 * | 12/2004 | Hayes et al. ............. 623/22.28 |
| 6,976,999 B2 * | 12/2005 | Charlebois et al. ...... 623/16.11 |
| 2003/0050705 A1 | 3/2003 | Cueille et al. ........... 623/22.24 |
| 2003/0074077 A1 | 4/2003 | Taylor ..................... 623/22.26 |
| 2003/0105529 A1 | 6/2003 | Synder et al. ........... 623/22.24 |
| 2005/0203634 A1 * | 9/2005 | Bassik et al. ............ 623/22.42 |

FOREIGN PATENT DOCUMENTS

| | | | |
|---|---|---|---|
| EP | 1025815 A1 | * | 8/2000 |
| GB | 2358353 A | * | 7/2001 |
| WO | WO2004/080353 A1 | * | 3/2004 |

* cited by examiner

VIEW XX

VIEW ZZ

Acetabula Spherical Reamer Head

Diameter Sized for 0.75 mm – 1.2 mm
Interference fit
with Canine Actabular Cup

CANINE ACETABULAR CUP

BACKGROUND OF THE INVENTION

1. Field of the Invention

The present invention relates to a cementless acetabular cup for canine hip replacements; and, more particularly, to an acetabular cup having an inner surface in sliding contact with a femoral head and an outer surface firmly bonded to underlying bone cavity, for providing both initial stability immediately after surgery and long-term stability.

2. Description of the Prior Art

Many patents address issues related to hip replacement, and more particularly to acetabular cup replacement devices. These patents disclose methods for attaching the acetabular cup into a bone cavity using cements of various formulations or screws and barbs in cementless procedures. A number of these patents address primarily human hip replacements, while a few of the patents are directed to canine hip replacement. There exist significant differences between acetabular cups designed for human hip replacement and those used for canine hip replacement. These differences are in large part occasioned by the larger overall weight of a human body, as compared to that of a dog. They also result from the additional attachments needed for human hip replacement devices, and the structure needed the enhanced movement requirements of a dog, which oftentimes spreads his hind legs when lying on its stomach. Accordingly, the geometry of an acetabular cup appointed for canine use is required to be different.

U.S. Pat. No. 4,666,450 to Kenna discloses an acetabular cup assembly prosthesis. The prosthesis comprises, in combination, a support shell for introduction into an acetabulum and a socket insert in nesting engagement within the shell. A support shell is composed of a Co—Cr—Mo alloy. A socket insertis composed of a high-density polyethylene. Both the shell and the anchoring posts are held in a tight fit. Methyl methacrylate is used as a cement, with the result that the device disclosed by the patent is not a cementless acetabular cup assembly prosthesis.

U.S. Pat. No. 4,715,860 to Amstutz discloses porous acetabular hip resurfacing. The device is appointed for human use. An acetabular cup has an outer diameter of 46 to 51 mm and uses a titanium shell with plastic insert. The polyethylene insert is prevented from rotation by use of a pin and metal tabs as well as a peripheral recess. This arrangement relies on point contact between the plastic insert and the titanium shell. It is incapable of preventing movement of the insert with respect to the titanium shell due to flexing of the plastic insert under load. In addition, the cylindrical portion at the sidewall is used to anchor the cementless porous acetabular cup in the bone cavity; the titanium shell is not tightly fitted in the bone cavity. Thus, the titanium shell may rotate within the bone cavity, compromising initial stability. Moreover, bonding of the porous layer applied is oftentimes not coherent. A metallic ring is relied upon to prevent the spilling or dislodgment of the sintered powder compact when the porous acetabular cup is inserted. The acetabular cup disclosed by the '860 patent is appointed for human, not canine use.

U.S. Pat. No. 4,904,265 to MacCollum discloses a cementless acetabular implant for human use, wherein the pelvis is eroded and requires rebuilding. A rigid metallic hemispherically shaped support cup is adapted for contiguous reception with the bone within the acetabular cavity. Reliance is placed on proper drilling of a bone cavity in an excessively eroded bone. The implanted device is progressively matched with the bone cavity. The acetabular cup is attached using a plurality of screws, and relies on these screws to provide initial stability. No disclosure is contained within the '265 patent concerning a canine acetabular cup.

U.S. Pat. No. 5,047,056 to Kenna discloses a canine hip prosthesis. The disclosure is directed to the femoral portion of a canine prosthesis. Use of a porous coating is said to result in superior bone ingrowth. No disclosure is contained by the '056 patent concerning a canine acetabular cup.

U.S. Pat. Nos. 5,226,917 and 5,310,408 to Schryver discloses an acetabular prosthesis with anchoring pegs. The acetabular cup prosthesis has a cup body with a plurality of bores extending between an inner concave surface and an outer convex surface. The bores function as drill guides for providing alignment in the drilling of surgical openings after the acetabular cup body is placed in a patient. The cup body has a porous coating, but is not held in place by interference. Rather, in accordance with teaching of the patents, the cup body is held in place by many drilled pegs, which firmly attach the cup body to the bone. Intimate contact is thereby provided between the cub body and cavity drilled bone. No disclosure is contained within the '914 and '408 patents concerning the cup body's compostion.

U.S. Pat. Nos. 5,290,315 and 5,370,704 to DeCarlo discloses an oblong acetabular cup wherein the plane of the opening into the cavity is skewed relative to the longitudinal plane of the prosthesis. With this arrangement, there is achieved adduction correction, anteversion correction, or both adduction and anteversion correction. This device is for humans with failed hip joint due to loosening of the spherical bone cavity, and requires an oblong acetabular cup. Surgical instruments and surgical methods for implanting the prostheses are disclosed. This correctable acetabular cup is not attached to the bone cavity by use of screws drilled through apertures. The plastic insert is not permanently attached to a block body and is movable by different adjusting elements. This human acetabular cup is appointed for use when the bone cavity is damaged. It is not a canine acetabular cup.

U.S. Pat. No. 5,549,701 to Mikhail discloses an acetabular cup for use by humans in direct-cemented implantation with the bone, or as an insert for a metal shell component of an acetabular cup assembly. This human hip device has a shell, which is attached to a bone with reamed cavity using screws and cement. The high molecular weight polyethylene polymeric cup is attached to the metal shell by means that comprise a pair of dovetail slots, each having a rear wall. Attachment of the cup to metal shell is not permanent. Bone cement and screws that drill into the bone are used to attach the acetabular cup. No disclosure is contained by the '701 patent concerning a canine acetabular cup.

U.S. Pat. No. 5,766,260 to Whiteside discloses an acetabular device for a hip replacement system having an acetabular shell, and a liner having a seal for insertion into the acetabular shell. Upon insertion of the liner into the shell, the annular ridges of the liner come into sealing engagement with the smooth tapered surface of the shell, preventing migration of debris along an interface of the liner with the shell. The liner is provided with several peripheral tabs, which produce an interference fit with several peripheral notches in the shell. A positive engagement is thereby provided to hold the liner in the shell as it bottoms therein. The metallic shell is attached to reamed bone cavity using screws; but is not attached by interference fit. Moreover, the polymeric liner is not firmly attached in any manner, and is not anchored to prevent torsional rotation. It is merely snapped into grooves in the metallic shell using projections in the liner. This is a hip joint replacement implant device for humans and is not appointed for canine use.

U.S. Pat. Nos. 5,874,123, 6,203,844 and 6,558,428 to Park discloses a polymeric prosthesis precoated with a bone cement compatible polymer, which can be polymethyl methacrylate. Once bonded to a polymeric prosthesis, the precoat strengthens the interface between a bone cement and a prosthesis, forming a stiffness gradient when the prosthesis is later implanted. The precoat is said to decrease the likelihood that the prosthesis will loosen and break away from the cement over time. The polymeric implant product appointed for use as an acetabular cup or a tibia plateau in replacing hip joints and knee joints respectively. No disclosure is made concerning cementless incorporation of the implant; the implant is not available for immediate usability, since time is needed for copolymerization.

U.S. Pat. No. 5,876,446 to Agrawal discloses a porous tissue-mating surface prosthesis. A biodegradable polymer impregnated within the interstitial spaces of the surface provides for enhanced rigid fixation and bony ingrowth. No disclosure is contained by the '446 patent concerning a canine acetabular cup.

U.S. Pat. No. 5,879,404 to Bateman discloses an acetabular cup and method for its manufacture. The acetabular cup has an outer shell and an inner liner that provides a bearing surface of metallic or ceramic material. A shoulder, formed around the rim of the inner liner, is made of a material that is softer than that used for the head or neck of a femoral component with which the acetabular cup is to be used. The shoulder limits the motion of the femoral component during use. It is composed of a polymeric material such as polyethylene. The polymeric shoulder of the outer shell is molded directly around the ceramic or metallic inner liner. The acetabular cup uses a polymeric outer shell, which comprises an inner liner of hard metallic or ceramic material and a soft polymeric lip. The polymeric outer shell is directly bonded to the bone cavity. No disclosure is contained by the '404 patent concerning a device for canine use. The device disclosed by the '404 patent does not provide immediate usability since the bond between the shell and bone cavity needs to cure.

U.S. Pat. No. 5,879,405 to Ries discloses an acetabular cup body prosthesis. The acetabular cup prosthesis has a cup body having inner convex and outer concave surfaces. The outer convex surface is not completely hemispherically shaped, but rather has a toroidal shape. A toroidal outer surface of the cup gradually thickens continuously from an apex toward a plurality of points designed to provide interference fit with a bone cavity reamed in a hemispherical shape. The oversized cup has either a toroidal geometry or a two-curvature geometry adapted to create an interference fit with the bone cavity. Interference between the acetabular cup and a spherical bone cavity is accomplished by either the toroidal geometry or the two-curvature geometry of the acetabular cup. Such interference alone is inadequate to securely attach the implant. Accordingly, the device uses screws to attach the acetabular cup. The size of the acetabular cup used in humans is large when compared with the quantum of interference (i.e. 1.25 mm) provided. The implant disclosed by the '405 patent requires an acetabular cup having a size (i.e. 40 mm to 80 mm) that is too large to be used as a canine acetabular cup.

U.S. Pat. No. 6,152,961 to Ostiguy discloses an acetabular prosthesis assembly with a shell component that is implantable within bone and a liner component that is matable to the shell. A groove is formed in the inner surface of the shell and one or more positive surface features are formed on the outer surface of the liner, adapted for selective mating with the groove of the shell. The liner may be joined to the shell by press fitting the two components together such that the positive surface features engage the groove. The shell is attached to the bone cavity by use of screws through a plurality of holes. Protrusions and ridges encourage attachment of the shell and are said to create ingrowth of bone tissue. The prosthesis assembly disclosed by the '961 patent is not a cementless attachment device; but relies instead on screws to hold the device in place. In addition there is no disclosure concerning a canine acetabular prosthesis assembly.

U.S. patent application Ser. No. 2003/0050705 to Cueille discloses an acetabular cup adapted for use in a total hip prosthesis. It comprises a prosthetic femoral head, sized to correspond to the anatomic head size of a natural femoral head, an inner bearing surface portion constructed from a ceramics material, and an outer titanium shell coated with a hydroxyapatite bone-interface layer. The acetabular cup cannot be used immediately after surgery since bone bond has to be developed prior to load application. Furthermore, the acetabular cup disclosed is not an implant device for canines.

U.S. Patent Application No. 2003/0074077 to Taylor discloses an acetabular prosthesis that comprises an outer portion with a concave inner surface and a convex outer surface; an inner portion within and spaced from the outer portion and having a concave inner surface defining a cavity and a substantially convex outer surface; and flexible connecting means, such as vanes connecting the outer convex surface of the inner portion to the concave inner surface of the outer portion. Such an acetabular prosthesis can exhibit matched compliance between the outer portion and the patient's pelvis while the inner portion accommodates idealized rigidity for artificial articulation components. Flexible vanes connect an outer shell with an inner shell in contact with the femoral head. This flexibility is said to provide idealized rigidity. The inner shell is not in interference fit or rigid attachment with the outer support shell in this arrangement. The device is suitable solely for humans, since large loads are flexibly supported.

There remains a need in the art for canine acetabular cups that can be implanted so that the device is usable immediately after surgery. Also needed is a canine acetabular cup that develops a long-term permanent bond between the implant and the underlying bone structure. Further needed is an acetabular cup device that provides increased flexibility capable of meeting the extended motion requirements of a dog. Even further needed is an implant device of the type described which functions throughout the lifetime of the dog without damage or deterioration.

SUMMARY OF THE INVENTION

The present invention provides a canine acetabular cup system that can be implanted so that the device is usable immediately after surgery. Once implanted, the canine acetabular cup develops a long-term permanent bond between the implant and the underlying bone structure. Advantageously, the acetabular cup of the present invention provides increased flexibility capable of meeting the extended motion requirements of a dog. In-service life of the device is maximized, causing the implant to function throughout the lifetime of the dog without damage or deterioration.

In accordance with the invention, there are provided multiple sizes of acetabular cups, which may be selected by a surgeon depending upon the size of the dog and its bone condition. For example, if a bone defect is observed during surgery, the surgeon may choose to enlarge the size of the bone cavity using a next size bone-reaming tool so as to accommodate a canine acetabular cup of the next size. The canine acetabular cup is provided to the surgeon at different sizes ranging from 24 mm to 32 mm, at 2 mm interval gradations. All acetabular cups match with a common sized, 17 mm femoral head. Therefore, acetabular cups of different sizes may be interchangeably used with common femoral hardware providing reliable hip replacement even when surgical situations become problematic.

Each of the acetabular cups is provided with a truncated cutout defining a 45 degree angle on one side of the cup so that the femoral hardware can have improved abduction and canine hip movement can occur over a larger range. The truncated cutout is oriented by the surgeon to face the direction where the extended movement is desired.

The acetabular cup is held in place by carefully controlled interference between a spherical, 4 stepped conical geometry and cylindrical Ti—Al—V shell member, and a reamed spherical bone cavity. An interference-fit is thereby created, which enhances attachment of the canine acetabular cup and imparts initial stability of the implant immediately after surgery. This interference also applies forces between the porous coating of sintered 250±50 μm (0.01±0.0025 inches) beads of chemically pure Ti on the outer surface of the Ti—Al—V shell member and the bone, and maintains intimate contact encouraging bone ingrowth. Excessive interference can cause the bone to fracture. Accordingly, the degree of interference must be very carefully controlled.

The multi-geometrical construct of this Ti—Al—V shell member is 1.2 mm thick, 2 mm with sintered porous beads attached. At up to 50 degrees from the apex, it has a spherical diameter that is the same as that of the bone cavity created by the reamer, thus providing zero interference. However, the interference increases progressively from zero to a full value of 0.7 to 1.2 mm, depending on the diameter of the canine acetabular cup and spherical reamer combination, as the angle from the apex of the geometry of the Ti—Al—V shell increases from 50 to 90 degrees. This is due to multiple conical segments and a cylindrical section of the Ti—Al—V shell.

An ultra high molecular weight (UHMW) polyethylene insert is attached to the interior surface of the Ti—Al—V shell member. Attachment is accomplished at the factory using an interference fit. Also, there are additional locking features that prevent the rotational, horizontal and vertical displacements of the UHMW polyethylene insert with respect to the Ti—Al—V shell member. The first locking feature preventing rotational movement comprises a non-circular cylindrical opening of 6 mm×3.8 mm at the apex of the Ti—Al—V shell member which mates with a corresponding non-circular post at the apex of the UHMW polyethylene insert. The second locking feature comprises a groove in the outer surface of the UHMW polyethylene insert that mates with a corresponding interior projection in the Ti—Al—V shell member preventing horizontal and vertical movement.

Since several diameters of canine acetabular cups are made available to the surgeon, and all canine acetabular cups mate with a common diameter femoral head, the thickness of the UHMW polyethylene insert is thicker in the larger diameter canine acetabular cup. Generally, the thickness of the UHMW polyethylene insert ranges from 2.4 mm to 6.4 mm. The UHMW polyethylene insert has a lip that cover the entire basal surface of the Ti—Al—V shell member, preventing contact of the Ti—Al—V shell with femoral components. The lip has an inclination of 51 degrees at the Ti—Al—V shell basal surface and the UHMW polyethylene insert has a matching inclination. Metal to metal rubbing action produces frictional debris and destroys the hip joint and this is prevented.

Broadly speaking, the canine acetabular cup is fitted in a spherical reamed bone cavity by controlled interference without use of cement, nails, screws or additional features to the titanium shell. The porous rough exterior surface of the Ti—Al—V shell of the canine acetabular cup provides enhanced friction. The same interference provides intimate contact between the bone surface and the porous coating on the Ti—Al—V shell, encouraging bone ingrowth. The Ti—Al—V shell is attached to the UHMW polymeric insert by interference and locking features, so that the UHMW polymeric insert does not move relative to the Ti—AL—V shell. Regardless of the size of the canine acetabular cup, it mates with a common size femoral head providing interchangeability between different sized acetabular cups and the femoral head.

BRIEF DESCRIPTION OF DRAWINGS

The invention will be more fully understood and further advantages will become apparent when reference is had to the following detailed description and the accompanying drawings, in which.

DESCRIPTION OF THE PREFERRED EMBODIMENTS

Figure 1A:
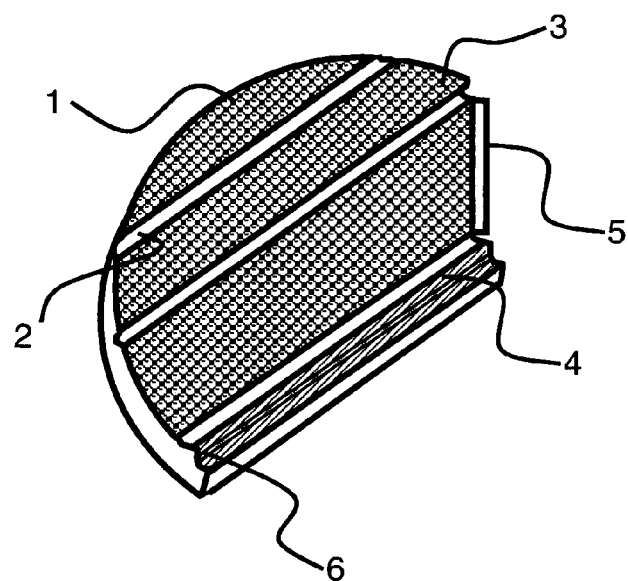
FIG. 1a and FIG. 1b are schematic views depicting the canine acetabular cup in an assembled condition, the two views provided illustrate the basic features of the cup.

The present invention provides an acetabular cup for canine hip replacements. The acetabular cup comes in a range of sizes comprising 24 mm, 26 mm, 28 mm, 30 mm and 32 mm, which are adapted for association with a common femoral head having a diameter of 17 mm. The surgeon may choose the size of the acetabular cup based on the bone size of the dog. If for any reason, a sized acetabular cup will not fit properly into an existing reamed cavity the next size of acetabular cup may be used by selecting the next reamer size, creating a hip implant that matches the femoral head and femoral prosthesis. In this manner, the canine acetabular cup system provides a variety of acetabular cup sizes that match precisely with a 17 mm femoral head, enabling reliable hip replacement procedures. In addition, each of the acetabular cups has a 45 degree cutout truncated section in one side thereof. Advantageously, the truncated cutout section enables extended hip motion in the cutout direction, allowing the dog to sit on its stomach while extending the hind legs.

The present canine acetabular cup is especially suited for use in cementless hip replacement procedures wherein an acetabular cup composed of an outer Ti—AL—V shell with a porous coating and an inner polyethylene liner is interference press fitted into a bone cavity using a cementless fixation procedure. The interference is carefully controlled so that the porous coating of the implanted acetabular cup makes intimate contact with the bone encouraging long term bone ingrowth. Due in part to the carefully controlled interference between the reamed bone cavity and the acetabular cup, and the reduced body weight of a dog, the implanted device is available for use immediately after surgery. Based on clinical and research results, it has been established that during this initial stability phase there must be less than 150 µm of motion between the acetabular cup and the bone to allow the bone an opportunity to grow into the pores of the outer surface of the shell. Motion exceeding this threshold during the initial stability phase of the procedure has been shown to result in fibrous tissue ingrowth in the porous outer surface. This, in turn, can result in loosening of the joint components and revision surgery. The motion of the acetabular cup in the acetabular cup system is limited to well below the 150 µm limit due to the carefully controlled interference fit and the friction provided by the porous coating of sintered chemically pure titanium beads on the outer surface of the Ti—Al—V acetabular cup shell. Long term stability is thus assured by intimate contact between the porous surface of the implanted device and the underlying bone.

The convex outer surface of the Ti—Al—V shell is coated with titanium beads, typically 250 µm±50 µm (0.01±0.0025 inches), which are sintered to the Ti—Al—V cup shell, maintaining porosity between the beads. The coating typically has a thickness of 0.8 mm (0.030 inches). The Ti—Al—V shell is typically 2 mm thick with the sintered titanium beads attached. The outer dimensions of the Ti—Al—V shell is chosen so that it produces an interference fit with a specially milled cavity in the bone where the Ti—Al—V shell will be placed, with an interference of 0.75 to 1.2 mm across the diameter. The outer convex surface of the Ti—Al—V shell is multiply curved to bring the above interference from zero at an angular location of 50 degrees from the apex to 0.75 to 1.2 mm at 90 degrees from the apex. This increasing interference along the distance from the apex allows intimate contact between the bonded chemically pure sintered Ti beads and the bone, resulting in rapid bone ingrowth development. This interference as well as the rough outer surface of the Ti—Al—V shell increases the friction between the bone and the Ti—Al—V shell, preventing the movement of the implant within the bone cavity, and permits use of canine legs immediately after surgery.

The articular inner surface of the acetabular cup comprises an UHMW polyethylene ASTM F-648 insert that is permanently pre-assembled at the factory and is held in place within the acetabular cup without any possibility of rotational, lateral or vertical displacement. The UHMW polyethylene insert also provides for long-term success by providing sufficient thickness for wear and an assembly, which resists disassociation. If insert assembly is inadequate, it can lead to excessive motion between the insert and shell, producing wear debris and eventual loosening through wear debris-induced osteolysis. The mechanical lock between the insert and shell must resist torsional fatigue and offset loading, which could be induced through neck impingement with the femoral stem in extreme ranges of motion.

The UHMW polyethylene insert has a typical thickness of 2.4 mm to 6.4 mm (0.1 to 0.25 inches) based on the size of the acetabular cup. Insert thickness is sufficient to withstand wear during normal operation of the acetabular cup over the dog's lifetime. The UHMW polyethylene insert is locked into the Ti—Al—V shell by use of an elongated post, which is not circular in cross section. The elongated post, which is 0.24 inches long and 0.155 inches wide having full radius in the UHMW polyethylene insert, mates with a corresponding elongated opening located in the dome of the Ti—Al—V cup shell, thus preventing relative rotational movement of the UHMW polyethylene insert within the Ti—Al—V cup shell. In addition, a retaining groove milled into the UHMW polyethylene insert, mates with a corresponding interior projection in the Ti—Al—V shell preventing lateral or vertical movement of the UHMW polyethylene insert with respect to the Ti—Al—V shell, even when high loads are applied during the lifetime use of the canine acetabular cup. Insertion of the UHMW polyethene insert into the Ti—Al—V cup shell is possible due to the elastic compliance of the UHMW polyethylene insert which can be pressed into the Ti—Al—V cup shell. Also, the dimensions of the UHMW polyethylene insert are chosen so that a general interference fit exists between the outer surface of the UHMW polyethylene insert and the concave inner surface of the Ti—Al—V cup shell. The UHMW polyethylene insert essentially has a lip that completely surrounds the outer edge of the Ti—Al—V cup shell, preventing metal to metal contact between the Ti—Al—V cup shell rim and a femoral head that is placed within the UHMW polyethylene insert. The lip also adds to the stability of retention of the UHMW polyethylene insert against the Ti—Al—V cup shell.

The face of the Ti—Al—V shell and the UHMW polyethylene insert are chamfered at 51°. This avoids point contact between the acetabular cup and the femoral stem in extreme ranges of motion as demanded by certain motions such as when a dog spreads his hind legs while lying on his stomach.

Figure 1B:
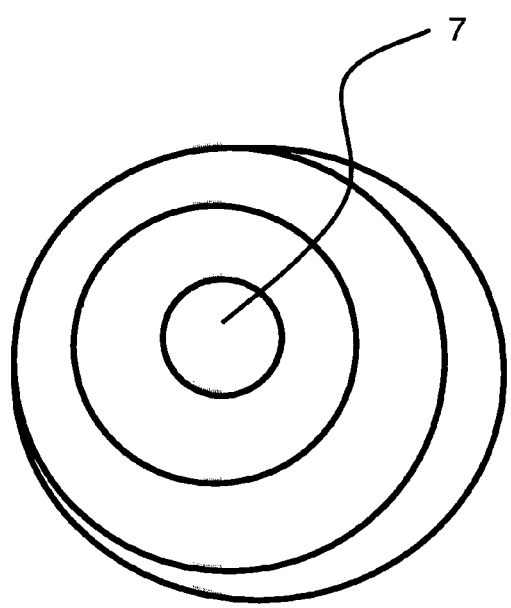

The manufactured canine acetabular cup, which has the UHMW polyethylene insert permanently attached to the Ti—Al—V cup shell at the factory, is produced in various sizes that match the requirements of dogs. Typically, the outer diameter of the canine acetabular cup is 24, 26, 28, 30, or 32 mm. The inner diameter of the UHMW polyethylene insert is always maintained at 17 mm to allow mating with a 17 mm femoral head. Since the thickness of the Ti—Al—V shell is always 1.2 mm, the thickness of the UHMW polyethylene insert is a function of the diameter of the canine acetabular cup and varies from 2.4 to 6.4 mm, the larger thickness corresponding to a larger diameter canine acetabular cup. Bone drilling cutters are provided for each size of the canine acetabular cup, and result in interference of 0.75 mm to 1.2 mm across the diameter. Larger interference is used for a larger diameter bone cavity. The cutting tool for creating the cavity in the bone has four tool inserts, which cut out the spherical bone cavity to the required dimensions., FIG. 1*a* is a schematic view depicting the side view and FIG. 1*b* is a schematic view depicting the top view of the canine acetabular cup in an assembled condition, illustrating the basic features of the cup. The Ti—Al—V shell 1 is shown with chemically pure sintered titanium beads 3 on the surface of the Ti—Al—V shell. A UHMW polyethylene insert 4 is placed within the Ti—Al—V shell, pre-assembled at the factory.

Figure 2:
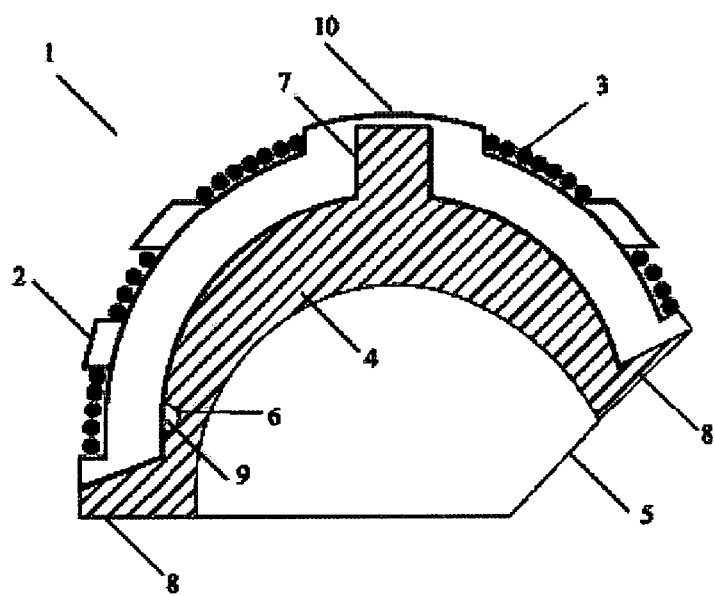
FIG. 2 is a schematic diagram depicting the canine acetabular cup in an assembled condition.

FIG. 2 is a schematic diagram depicting the canine acetabular cup in an assembled condition. A truncated section 5 of the canine acetabular cup is created for increased abduction of the hip joint, a feature that provides enhanced movement of the hip joint which is necessary to accommodate the movement requirements of a dog. A groove 6 on the UHMW polyethylene insert 4 mates with a interior projection 9 on the Ti—Al—V shell preventing lateral or vertical movement of the UHMW polyethylene insert with respect to the Ti—Al—V shell. A non-circular post 10 in the UHMW polyethylene insert mates with an elongated opening 7 in the T—Al—V shell preventing rotational movement of the insert within the shell. The UHMW polyethylene insert has a lip 8 on the basal plane surface of the polyethylene insert preventing contact between femoral components and the Ti—Al—V shell.

Figure 3A:
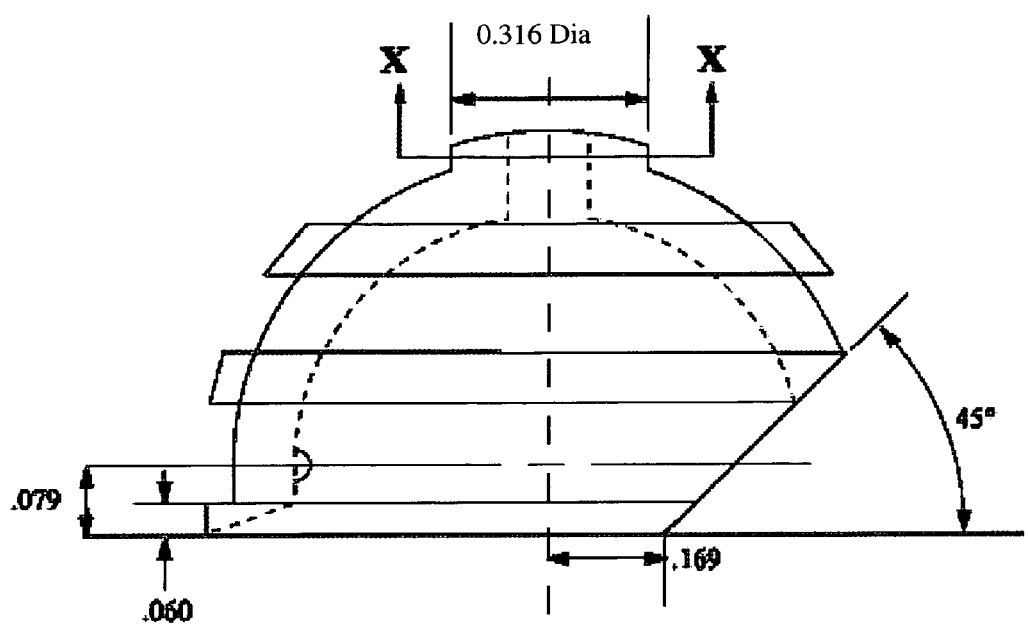
FIG. 3a is a frontal view of the canine acetabular cup detailing the non-circular cylindrical opening at the apex of the Ti—Al—V shell.
Figure 3B:
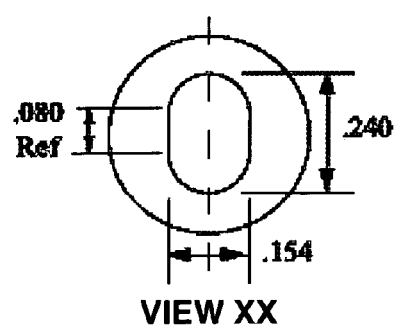
FIG. 3b is the frontal view of the canine acetabular cup of FIG. 3a taken along line XX, detailing the non-circular cylindrical opening at the apex of the Ti—Al—V shell.

FIG. 3a is an engineering drawing detailing the dimensions and construction of a typical Ti—Al—V shell 1. FIG. 3b is the frontal view of the canine acetabular cup of FIG. 3a taken along line XX, detailing the non-circular cylindrical opening at the apex of the Ti—Al—V shell. The shell is manufactured with an outer dimension to mate with a reamed bone cavity having a diameter of approximately 24, 26, 28, 30 and 32 mm, with an interference of 0.75 to 1.2 mm (0.03 inches to 0.05 inches) measured at the basal plane of the canine acetabular cup, with larger interference associated with larger diameter canine acetabular cups. The interference is zero at 50 degrees from the apex of the Ti—Al—V shell and increases to full value at 90 degrees from the apex. Thus, the outer surface of the shell has multiple curvatures with the maximum interference occurring closer to the basal plane of the canine acetabular cup. The shell is made from Ti—Al—V or cobalt chrome, tantalum alloy with typical wall thickness of 1.2 mm (0.05 inches). The chemically pure titanium beads, sintered on the outer surface of the shell and held in between the circumferential ribs has a dimension of 250±50 µm (0.01±0.0025 inches). The apex of the Ti—Al—V shell comprises an elongated cylindrical opening, which is 6 by 3.8 mm (0.240 inches by 0.152 inches). This opening is adapted to receive a cylindrical post in the polyethylene insert to prevent the rotational movement of the polyethylene insert with respect to the Ti—Al—V shell. In addition, the inner surface of the shell has an interior projection at a distance of 4 mm (0.159 inches) from the base surface of the Ti—Al—V shell that mates with a groove in the polyethylene insert and locks it, preventing horizontal or vertical movement. The edge of the shell at the bottom surface is tapered to accept the polyethylene insert. The right side of the cup is cut out to produce a truncated section at the 45 degree angle, as shown, to provide increased movement of the hip joint in the plane of the drawing.

Figure 4A:
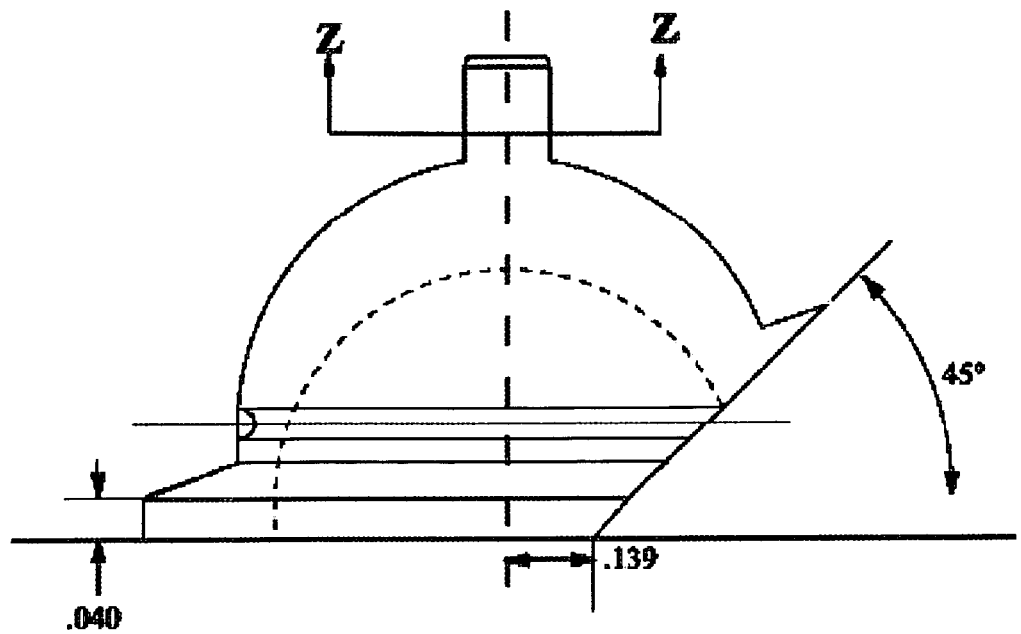
FIG. 4a is a frontal view depicting the design and dimensions of the UHMW polyethylene insert and the details of the non-circular cylindrical post at the apex.
Figure 4B:
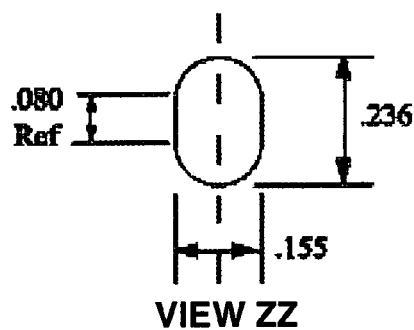
FIG. 4b is a frontal view of FIG. 4a taken along line ZZ, depicting the design and dimensions of the UHMW polyethylene insert and the details of the non-circular cylindrical post at the apex.

FIG. 4a is an engineering drawing detailing the dimensions and construction of a typical UHMW polyethylene insert 4. FIG. 4b is a frontal view of FIG. 4a taken along line ZZ, depicting the design and dimensions of the UHMW polyethylene insert and the details of the non-circular cylindrical post at the apex. The polymeric insert has a cylindrical post at the apex which is 6 mm by 3.8 mm (0.236 inches by 0.155 inches) and is designed to mate with the elongated opening in the Ti—Al—V shell. The external surface of the polyethylene insert has a groove which mates with the circumferential rib or projection on the interior surface of the shell. The inner surface of the polyethylene insert has a dimension of 17 mm (0.68 inches) regardless of its outer dimension or shell size and is designed to engage with a 17 mm femoral head. The polyethylene insert has a wear thickness of 2.4 to 6.4 mm (0.1 to 0.2 inches) depending on the overall size of the canine acetabular cup. A larger size canine acetabular cup has a larger polyethylene insert wear thickness, since it mates with a common diameter femoral head of 17 mm (0.68 inches). The bottom edge of the polyethylene insert has a lip which mates with the taper in the Ti—Al—V shell, thus covering the entire surface of the shell and preventing metal to metal contact between the femur hardware and the Ti—Al—V shell. The right side of the polyethylene insert is cut out to create a truncated section at 45 degrees as shown in FIG. 4. There is a corresponding truncated section at 45 degrees cut out of the Ti—Al—V shell. The truncated section provides extended movement of the canine femur.

Figure 5:
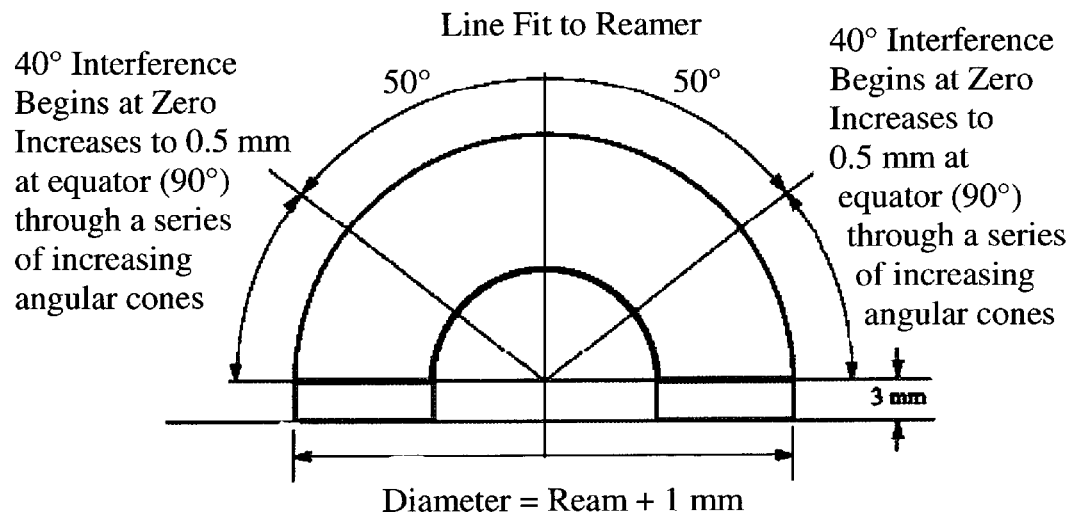
FIG. 5 is a diagrammatic representation depicting parameters required to achieve an interference fit between Ti—Al—V shell member and the reamed bone cavity.

FIG. 5 diagrammatically depicts parameters required to achieve an interference fit. The Figure shows a cross section perpendicular to the sheet of the drawing of FIGS. 3a, 3b, 4a and 4b, taken along the lines X—X and Z—Z. The reamed bone cavity precisely matches the 26 mm Ti—Al—V shell for 50 degrees from apex with no interference. The interference increases from this zero value to 1 mm interference as the angle is increased from 50 to 90 degrees from the apex, 1 mm being the interference value for a 26 mm Ti—Al—V shell. The Ti—Al—V shell has a 3 mm cylindrical section where the interference is fully maintained.

Figure 6:
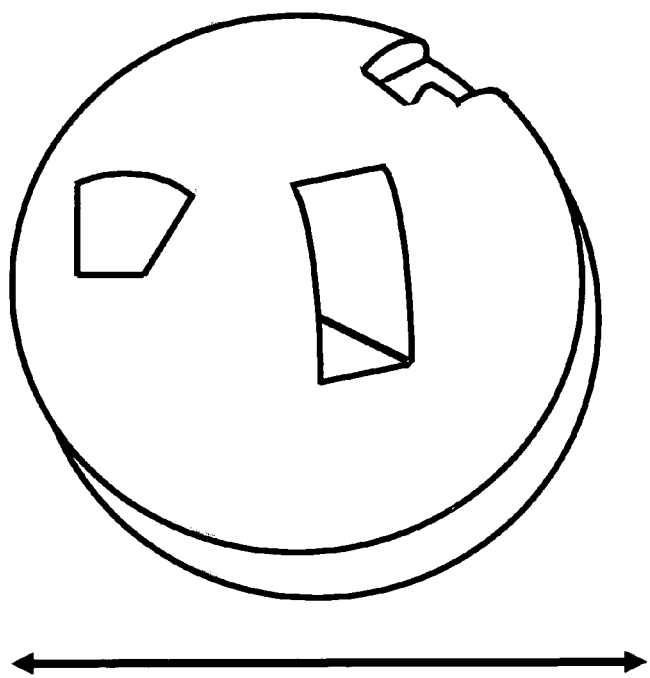
FIG. 6 is a diagram illustrating the head of an acetabular spherical reamer.

FIG. 6 is a diagram illustrating the head of an acetabular spherical reamer. Reamers are provided for each size of the canine acetabular cup, and are especially shaped to precisely machine out spherical cavities of 24, 26, 28, 30 and 32 mm. These cutters overlap and ream out a spherical bone cavity.

The key features of the canine acetabular cup are:
1. a canine acetabular cup having a cutout truncated section at 45 degrees, for increased abduction to provide enhanced movement of the canine hip joint that meets the movement requirements of a dog;
2. a spherical dome of the T-Al—V shell encompassing a 50° arc to either side of centerline; which mates with a line-to-line fit with the bone preparing spherical reamer;
3. a section below the dome, which is composed of multi-conical sections adapted to provide a gradually increasing interference fit with the spherically prepared bone; each of the sections beginning at 50° and continuing through 90°, and the interference beginning at zero and increasing to 0.75 mm to 1.2 mm depending on the tolerances between the implant and instruments;
4. a section below the conical sections, which is a cylinder and has a designed interference with the bone preparation of 0.75 mm to 1.2 mm, depending on the tolerances between the implant and instruments;
5. a truncated section of the conical and cylindrical sections, which provides for increased abduction (i.e. increased range of motion when the dog spreads his hind legs and lies on its stomach); and
6. a circumferential groove disposed within the cylindrical section, that assists the insert to lock onto the cup and provides for a stable and controllable insertion of the polyethylene insert.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A canine acetabular cup system, comprising:
 a. a plurality of different sized acetabular cups for selection by a surgeon, said acetabular cups being adapted for use with a common-sized femoral head;
 b. each said acetabular cups being provided with a truncated cutout on one side thereof for improved abduction and canine hip movement;
 c. said acetabular cup adapted to be held in place within a reamed spherical bone cavity by controlled interference between a multiple curvature Titanium-Aluminum-Vanadium shell of said acetabular cup and the bone cavity, providing for frictional attachment of the canine acetabular cup and imparting initial stability to the implant immediately after surgery;
 d. said shell having a porous coating of chemically pure Titanium beads sintered between circumferential rings on the outer surface of said shell, to increase friction at contact surfaces with the reamed bone cavity, promote bone growth and provide for long term stability of the implant;
 e. said shell having an ultra high molecular weight polyethylene insert attached within the shell by an interference fit, having locking features that prevent rotational, horizontal and vertical displacements of the said polyethylene insert with respect to the said shell;
 f. said locking feature comprising a non-cylindrical opening at an apex of said shell to receive and mate with a corresponding non-circular post at the apex of said polyethylene insert thereby preventing relative rotation of said polyethylene insert with respect to said shell;
 g. said locking feature comprising a groove in said polyethylene insert that mates with a corresponding interior projection of said shell, thereby preventing horizontal and vertical movement;
 h. said polyethylene insert having a spherical opening to receive said common-sized femoral head; and
 i. said polyethylene insert having a lip covering the basal surface of said shell, preventing contact between said common-sized femoral head and said shell.

2. A canine acetabular cup system as recited by claim 1, wherein said plurality of multi-sized acetabular cups have nominal diameters adapted to produce an interference fit with different-sized spherical reamed bone cavities, the diameters of said acetabular cups being approximately 24, 26, 28, 30 and 32 mm.

3. A canine acetabular cup system as recited by claim 1, wherein said truncated cut out is at an angle of 45 degrees from the basal plane and is off set from the center of said shell member.

4. A canine acetabular cup system as recited by claim 1, wherein said controlled interference is provided by gradually increased interference between said shell and the spherically reamed bone cavity, said interference being extant at angular locations about 50° to 90° from said apex.

5. A canine acetabular cup system as recited by claim 1, wherein said porous coating of 250 ±50 μm (0.01 ±0.0025 inches) beads of chemically pure Titanium beads has a thickness of 0.8 mm (0.030 inches).

6. A canine acetabular cup system as recited by claim 1, wherein said cylindrical opening at the apex of said shell has a dimension of 6 by 3.8 mm (0.240 inches by 0.152 inches).

7. A canine acetabular cup system as recited by claim 1, wherein said polyethylene insert has a thickness ranging from 2.4 mm to 6.4 mm (0.1 to 0.2 inches) based on the size of the acetabular cup.

8. A canine acetabular cup system as recited by claim 1, wherein said common size femoral head has a diameter of 17 mm.

* * * * *